United States Patent
Okamoto et al.

(10) Patent No.: US 6,869,681 B2
(45) Date of Patent: Mar. 22, 2005

(54) FUNCTIONAL COMPOSITION, FUNCTIONAL RESIN COMPOSITION, AND FUNCTIONAL MOLDING

(75) Inventors: Hiroshi Okamoto, Owari-asahi (JP); Shin-ichi Inoue, Tokoname (JP); Tetsuo Kanagawa, Otsu (JP); Masataka Sano, Hamamatsu (JP); Hiroki Miyamatsu, Hamamatsu (JP); Kimi Yoshida, Hamamatsu (JP)

(73) Assignee: Kabushiki Kaisha Erubu, Hammatsu (JP)

( * ) Notice: Subject to any disclaimer, the term of this patent is extended or adjusted under 35 U.S.C. 154(b) by 233 days.

(21) Appl. No.: 09/771,700

(22) Filed: Jan. 30, 2001

(65) Prior Publication Data

US 2001/0023018 A1 Sep. 20, 2001

(30) Foreign Application Priority Data

Feb. 2, 2000 (JP) .............................. 2000-025730

(51) Int. Cl.$^7$ ............................ D02G 3/00; B32B 5/16; C04B 9/02; C09D 5/14; C01B 3/00
(52) U.S. Cl. .................. 428/373; 428/325; 428/331; 428/411.1; 106/14.44; 106/15.05; 252/188.28
(58) Field of Search ................ 428/323, 324, 428/325, 326, 331, 370, 373, 411.1; 106/14.05, 14.44, 15.05; 252/188.1, 188.28; 523/102; 524/72

(56) References Cited

U.S. PATENT DOCUMENTS

| | | | | |
|---|---|---|---|---|
| 5,830,567 A | * | 11/1998 | Panush | 428/324 |
| 6,156,817 A | * | 12/2000 | Okamoto et al. | 523/102 |
| 6,211,500 B1 | * | 4/2001 | Cochran, II et al. | 219/725 |
| 6,423,408 B2 | * | 7/2002 | Okamoto et al. | 428/370 |
| 6,465,114 B1 | * | 10/2002 | Honda et al. | 428/659 |

* cited by examiner

Primary Examiner—Sheeba Ahmed
(74) Attorney, Agent, or Firm—Armstrong, Kratz, Quintos, Hanson & Brooks, LLP

(57) ABSTRACT

A functional composition, in which an increase in particle size due to secondary flocculation of particles in a mixed system of a plant-originated functional component (A) and a ceramics component (C) is effectively prevented; a functional resin composition made of the functional composition, which can be applied to various utilities; and a functional molding made of the functional composition, which is superior in deodorizing properties, antimicrobial properties, moldability, post-processing properties such as stretching properties, physical properties, are provided. The functional composition contains a mixture of a plant-originated functional component (A), a finely divided tabular mineral (T) having a low hardness and cleavage, and a ceramics component (C) other than the mineral (T). The functional resin composition contains the foregoing components and a resin (R). The functional molding is made of a molding of the resin (R) having the foregoing components formulated thereinto. The functional molding may be a composite molding such as a core-sheath type.

10 Claims, 8 Drawing Sheets

(A)

(B)

(A)

(B)

(A)

(B)

(A)

(B)

(A)

(B)

(A)

(B)

(A)

(B)

(A)

(B)

FUNCTIONAL COMPOSITION, FUNCTIONAL RESIN COMPOSITION, AND FUNCTIONAL MOLDING

BACKGROUND OF THE INVENTION

1. Field of the Invention

The present invention relates to a functional composition having properties such as deodorizing properties and antimicrobial properties, which comprises a plant-originated functional component and a specified mineral component. Also, the present invention relates to a functional resin composition and a functional molding, each containing the functional composition.

2. Description of the Conventional Art

As filters to be incorporated into air conditioners or air cleaners, filters made of a polypropylene filament that is not only advantageous from the standpoint of production cost but also superior in characteristics such as moldability, mechanical strength, waterproof properties, and chemical resistance, are widely used. It is also known that polypropylene for this filter is incorporated with a synthetic bactericide or carried with a catechin as a tea-extraction component, through external attachment or internal addition.

For example, Japanese Patent Laid-Open No. 99656/1989 mentions an antibacterial electret filter comprising polypropylene fibers having 0.1% or more of a bactericide incorporated therein. However, the bactericide that is used in the working examples of this patent publication is a thiabendazole as a synthetic bactericide.

Further, Japanese Patent Laid-Open No. 148407/1995 describes an antiviral filter comprising a filter impregnated with, or a filter material incorporated with, a virus-inactivating agent comprising, as an active ingredient, a tea-extraction component. The tea-extraction component as referred to herein means a tea polyphenol such as a catechin. In the working examples of this patent publication, there are given (A) an example in which the tea-extraction component is dissolved in water to prepare an aqueous solution, which is then impregnated in and attached to an electret filter; and (B) an example in which polypropylene is mixed with the tea-extraction component, and the mixture is molten to form a film, which is then cut and fabricated into a non-woven fabric.

Moreover, Japanese Patent Laid-Open No. 266828/1996 describes an antiviral filter comprising a dust-collecting filter and a filter impregnated with a tea-extraction component. The tea-extraction component as referred to herein means a tea polyphenol such as a catechin. Further, the filter having a tea-extraction component attached thereto as referred to herein means an electret filter, an HEPA filter, a high-performance filter, a middle-performance filter, a bag filter, etc.

In the case where the tea-extraction component is dissolved in water to prepare an aqueous solution, which is then externally impregnated and carried in a filter, namely, in the method of attaching and carrying by impregnation, the tea-extraction component is compatible with water, and hence, its fixing properties and waterproof properties are not sufficient. Therefore, when this filter is used on being brought into contact with water, or is used while being often washed with water, it involves such a defect that the tea-extraction component as an attaching component is readily lost.

In the method in which the tea-extraction component such as a catechin is internally added to (i.e., incorporated into) polypropylene as a filter material and then melt formed, since the tea-extraction component such as a catechin, which is originally soluble in water, is incompatible with polypropylene as a non-polar resin, it likely bleeds out onto the filament surface to generate stains. Further, when the filament is dipped in water or washed with water, a major part of the extraction component elutes out, whereby the effect is drastically reduced. Even when the internal addition amount is increased in consideration of the bleeding-out, the elution amount is still high during the contact with water. Accordingly, it is inevitable that not only the production cost is high, but also the spinning properties, drawing properties and strength are reduced. In addition, in this internal addition method, during the melt forming, a considerable amount of an effective part of the tea-extraction component is volatilized out, and hence, it is inevitable that the relatively expensive active ingredient is lost.

We, the present inventors found as follows. That is, when a specified ceramics component is co-existent during internal addition of a functional component such as a catechin and a saponin to a resin component, followed by forming, a mutual action is generated between the functional component and the ceramics component. As a result, the forming is carried out smoothly, the bleeding of the functional component onto the molding surface is inhibited and, even when the resulting molding is used on being brought into contact with water, the elution of the functional component is effectively inhibited. Then, we have filed separately an application for patent. Further, we found that when this technology is applied to an external component of a composite molding such as a composite filament, much more preferred results are obtained. Then, we have also filed an application for patent regarding this technology.

However, even according to the above-described technologies made by the present inventors, in the preparation step of mixed particles of the functional component and the ceramics component (especially, in the preparation step of composite particles of the both components) or in the resin phase during formulating the mixed particles into the resin, followed by forming, the particles caused secondary flocculation so that the particle size increased, and the internal addition of the mixed particles adversely affected the moldability, the post-processing properties (drawing properties, etc.), and the physical properties of the molding, whereby the desired function and effect were not sufficiently be obtained. If such a problem could be overcome, a molding having superior functionalities should be obtained. Further, when its solution means is utilized, it can be expected that these mixed particles are applicable to other uses than that for the molding.

SUMMARY OF THE INVENTION

Under these circumstance, the present invention is aimed to provide a functional composition which is capable of effectively preventing an increase in particle size of a mixed system of a plant-originated functional component and a ceramics component, caused by secondary flocculation of particles; a functional resin composition using the functional composition comprising the mixed particles, which can be applied to various uses; and particularly, a functional molding made of the functional composition comprising the mixed particles, having superior properties in deodorizing properties, antimicrobial properties, moldability, post-processing properties (drawing properties, etc.), and physical properties.

Specifically, the functional composition according to the present invention comprises a mixture of a plant-originated functional component (A), a finely divided tabular mineral (T) having a low hardness and cleavage, and a ceramics component (C) other than the finely divided tabular mineral (T).

The functional resin composition according to the present invention comprises a plant-originated functional component (A), a finely divided tabular mineral (T) having a low hardness and cleavage, a ceramics component (C) other than the finely divided tabular mineral (T), and a resin (R).

The functional molding according to the present invention comprises a molding of a resin (R) having formulated therein with a plant-originated functional component (A), a finely divided tabular mineral (T) having a low hardness and cleavage, and a ceramics component (C) other than the finely divided tabular mineral (T).

DETAILED DESCRIPTION OF THE INVENTION

Figure 1:
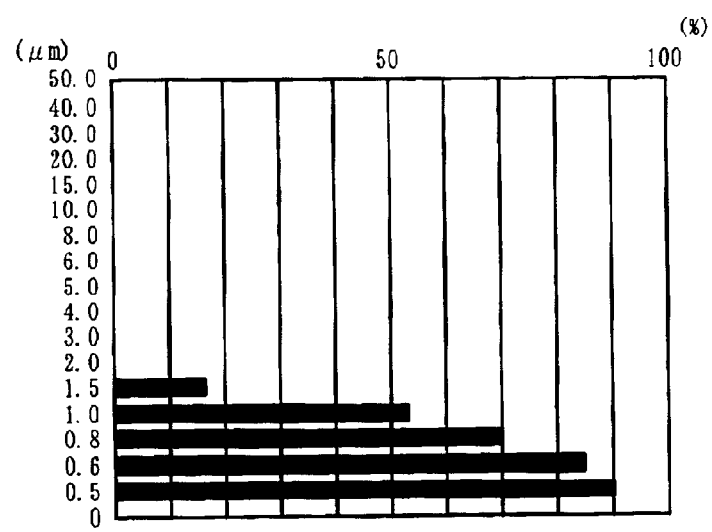
FIG. 1 is a graph showing the grain size distribution of the raw material talc ($T_1$)
Figure 1:
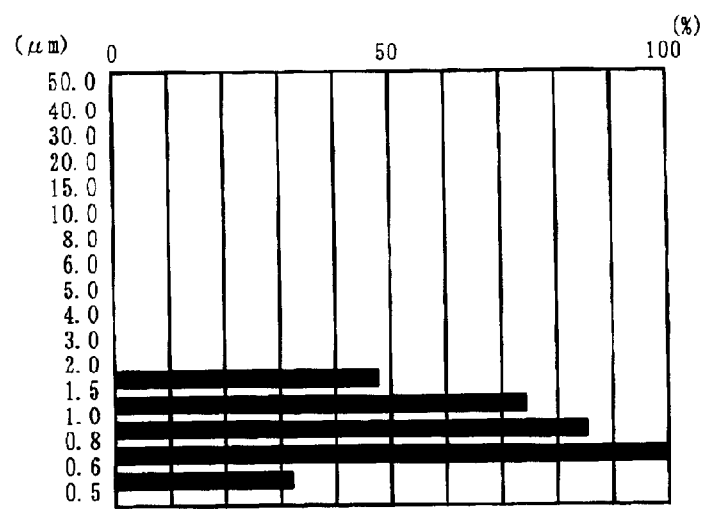

The present invention is described below in detail.
[Functional Composition]

As described above, the functional composition according to the present invention comprises a mixture of a plant-originated functional component (A), a finely divided tabular mineral (T) having a low hardness and cleavage, and a ceramics component (C) other than the finely divided tabular mineral (T).
(Functional Component (A))

As the functional component (A), various kinds of plant-originated materials are useful. A representative example of the functional component (A) is at least one member selected from the group consisting of a catechin, a saponin, a tea-leaf powder, a tea-leaf extract, and tannin (tannic acid). The catechin is important particularly. These are components having functionalities such as deodorizing properties (e.g., deodorizing properties, smell-eliminating properties, toxic gas-removing properties), antimicrobial properties (e.g., antibacterial properties, bactericidal properties, bacteriostatic properties, fungicidal properties, antiviral properties), physiological activity (e.g., antiallergic properties), and antioxidation properties. Besides, various plant essential oils and various plant extracts used for crude drugs or herb medicines can also be used as the functional component (A).

As the above catechin, catechin, monomeric and oligomeric ones (including theaflavin) are used. Those that are particularly important as the catechin to be used in the present invention are tea-originated catechin formulations in which the catechin concentration is increased. Major components of the catechin are epigallocatechin, epigallocatechin gallate, epicatechin, epicatechingallate, etc. Since these components are not required to be isolated from each other, a formulation containing the tea catechin in a high concentration, comprising a mixture of these components (preferably that containing 20% or more, and more preferably 25% or more of the tea catechin), can be suitably used as it stands. The tea-originated catechin formulation is readily available because the commercially available tea-originated catechin formulation includes 30% products, 50% products, 60% products, 70% products, 80% products, and 90% products. The tea includes not only green tea but also black tea as a fermented tea and oolong tea as a semi-fermented tea. For example, in the case of black tea, various kinds of theaflavin (black tea polyphenol) are prepared in the fermentation step from epigallocatechin, epigallocatechin gallate, epicatechin, and epicatechin gallate. Further, in the case of oolong tea, special catechin derivatives such as epigallocatechin-4-O-methyl gallate are included in addition to the four main catechins. The catechin is contained in various kinds of plants other than teas, such as catechu, and hence, catechins originated from such plants are also useful.

Among the saponins, tea saponin can be obtained by extracting a saponin-containing component with an organic solvent or water from tea leaves or tea seeds and then repeatedly purifying it by means of column chromatography, etc. Though the tea saponin includes steroid-based saponin and triterepenoid-based saponin, any of them can be used for the object of the present invention. Since the saponin is also contained in various kinds of plants other than teas, such as ginseng (ginseng radix), panacis japonici rhizoma, soybean (Glycine max MERR.), bupleurum root (bupleuri radix), hydrangeae dulcis folium, loofah (*Luffa cylindrica M. Roemen*), polygala root (polygalae radix), platycodon root (platicodi radix), senega (senegae radix), ophiopogon tuber (ophiopogonis tuber), akebia stem (*akebiae caulis*), anemarrhena rhizome (*anemarrhenae rhizoma*), achyranthes root (achyranthis radix), licorice root (glycyrrhizae radix), and smilax rhizome (*smilacis rhizoma*), saponins made from these plants can also be used.

Examples of the tea-leaf powder or tea-leaf extract which can be used include powders or extracts of teas, such as the first pick of tea, the second pick of tea, the third pick of tea, deeply steamed tea, kabusecha, black tea, and oolong tea.

As the tannin (tannic acid), commercially available purified tannic acid can be used. Extracts or semi-purified products of natural plants containing tannic acid, such as Chinese gallotannin and Turkish gallotannin, can be used as they stand.
(Finely Divided Tabular Mineral (T))

As the finely divided tabular mineral (T), tabular minerals having a low hardness and cleavage are useful. The low hardness as referred to herein means that a Mohs hardness is about 3.5 or less. The mean particle size is 5 $\mu$m or smaller, preferably 2 μm or smaller, more preferably 1.5 μm or smaller, and most preferably 1 μm or smaller, particularly in a sub-micron meter order (smaller than 1 μm). Namely, it is preferred that the particle size is as small as possible. Especially, those of a micro fine grade in a sub-micron meter order are recommendable. The mean particle size as referred to herein is one measured by the laser diffraction method.

Representative examples of the finely divided tabular mineral (T) having a low hardness and cleavage include talc and mica. Since it is not easy to micronize the mineral, when those of a micro fine grade are used, they are pulverized by various means. Alternatively, only those of a fine powder portion of pulverized materials are obtained by classification. Thus, it is intended to obtain those having a particle size as small as possible.

The talc as referred to herein is a pulverized material of a mineral, which is a white- to gray-colored, sliding inorganic powder having a fatty feeling. Although a chemical composition of talc slightly varies depending upon the place of production, it is basically represented by $4SiO_2.3MgO.H_2O$. A crystal structure of the talc is of a three-layered structure in which a surface is composed of silicic acid, a second layer is composed of magnesia having a hydroxyl group, and a third layer is composed of silicic acid, respectively. Because of this peculiar crystal structure, the talc is liable to be sliding and has a Mohs hardness of 1, which is the lowest value among inorganic minerals.

One of commercially available products which are successfully micronized is "SG-2000" made by Nippon Talc Co., Ltd., as talc having a mean particle size of 0.97 μm, and a few of overseas products are also available. When this product is further classified, one having a desired particle size can be prepared. Incidentally, it is said in the business field of talc that there is a limit called "a wall of 3 μm", and it is not easy to obtain talc having a particle size smaller than 3 μm on an industrial scale by the laser diffraction method. Much more, it has been considered to be impossible till quite recently to obtain talc in a sub-micron meter order.

As the mica, both natural and synthetic ones can be used, and specific examples include sericite, muscovite, phlogopite, fluorphlogopite, colored mica having a colored element coordinated in a crystal thereof, mica titanium, and UV light-absorptive mica. The Mohs hardness of mica is usually from about 2.5 to 3.2.

(Ceramics Component (C))

As the ceramics component (C), various kinds of ceramics other than the finely powdered tabular mineral (T) described above are useful. In this case, as described below in detail, a silica gel obtained via a hydrous silicate gel, a combination of an inorganic sintering aid and an inorganic flocculant, and a combination of ceramics particles (those other than the finely divided tabular mineral (T)—the ceramics particles may be sometimes referred to simply as "ceramics particles", hereinafter), an inorganic sintering aid and an inorganic flocculant are suitably used. When these ceramics are used, it is possible to realize complexation with the functional component (A) by utilizing of a flocculation force.

As the silica gel, a silica gel obtained via a hydrous silicate gel is suitably used. At this time, an aqueous solution of a silicate is mixed with an acid to adjust the pH, and the thus obtained hydrous gel is further washed with water to remove ions and then dried to obtain a desired silica gel. Examples of the silicate include sodium silicate represented by $Na_2O.nSiO_2$ and potassium silicate represented by $K_2O.nSiO_2$. The former sodium silicate being particularly important. A concentrated aqueous solution of the silicate is generally called as a water glass, and representative commercially available water glasses have an $SiO_2$ content of 22 to 38% by weight and an $Na_2O$ content of 5 to 19% by weight.

Examples of the inorganic sintering aid include polyvalent metal salts of an inorganic acid such as phosphoric acid, sulfuric acid, nitric acid, and carbonic acid, and fluorides or silicofluorides of an alkali metal or an alkaline earth metal. As the polyvalent metal salts, those of aluminum, zinc, magnesium, calcium, or manganese are suitably used. They are usually put into use in a state where a hydrous salt or hydrate is dissolved in water.

Suitable examples of the inorganic flocculant include inorganic flocculants in a state of sol or solution and particularly, silicic anhydride in a state of sol, or silicates (such as sodium silicate and potassium silicate) in a state of solution. The silicic anhydride in a state of sol includes not only usual colloidal silica that uses water as a medium but also an organosilica sol that uses an organic solvent such as an alcohol, as a medium.

Examples of the ceramics particles in the combination of ceramics particles, an inorganic sintering aid and an inorganic flocculant include various clay minerals, oxides, hydroxides, composite oxides, nitrides, carbides, silicides, borides, zeolite, cristobalite, diatomaceous earth, polyvalent metal salts of silicic acid and tourmaline. Examples of the clay minerals include kaolin, and bentonite. Examples of the oxides include alumina, titania, silica, zirconia, magnesia, and zinc oxide. Of those, zinc oxide itself has somewhat deodorizing property. Examples of the hydroxides include hydroxides of aluminum, zinc, magnesium, calcium, and manganese. Examples of the composite oxides include alum stone. Examples of the nitrides include silicon nitride and boron nitride. Examples of the carbides include silicon carbide and boron carbide. Examples of the polyvalent metal salts of silicic acid include aluminum salts, zinc salts, magnesium salts, calcium salts, and manganese salts.

With respect to the proportion of the respective components, in the combination of an inorganic sintering aid and an inorganic flocculant, in many cases, the amount of the inorganic flocculant is about 100 to 300 parts by weight in terms of solids content, or more, based on 100 parts by weight of the solids content of the inorganic sintering aid. And, in the combination of ceramics particles, an inorganic sintering aid and an inorganic flocculant, those amounts at which the ceramics particles as a major component as well as the inorganic sintering aid and the inorganic flocculant can play the respective roles are employed. In many cases, the amounts of the inorganic sintering aid and the inorganic flocculant are about 0.5 to 20 parts by weight and 0.5 to 25 parts by weight in terms of solids content, respectively based on 100 parts by weight of the ceramics particles.

As other examples of the ceramics component (C), clay minerals having a nature of swelling upon absorption of water, such as sepiolite, vermiculite, bentonite, sericite clay, and mica of a water-swelling grade, can be suitably used. Of these, sepiolite having a specific fibrous structure is particularly important.

Further, as the ceramics component (C), fine powders of ceramics particles such as silica, alumina, and titania can be used as they are.

(Composite Particles of Functional Component (A) and Ceramics Component (C))

It is preferred that the functional component (A) and the ceramics component (C) are used for the respective utilities after producing the composite particles of the both components. In this connection, though it is preferred to produce the composite particles in a state that the finely divided tabular mineral (T) is contained, this embodiment will be described later. Thus, the relationship between the functional component (A) and the ceramics component (C) is first of all described hereunder.

In the case where the composite particles are prepared, when the ceramics component (C) is a silica gel obtained via a hydrous silicate gel, it is desired that the functional component (A) is added to the system before, during or after mixing the aqueous solution of silicate and the acid but before the completion of the gelation reaction, thereby containing the functional component (A) in the silica gel. Thus, the ceramics can be flocculated in a state containing the functional component (A).

In the case where the ceramics component (C) is a combination of an inorganic sintering aid and an inorganic flocculant, it is preferred that the ceramics are flocculated in a state containing the functional component (A). One example is given below. An aqueous solution of aluminum phosphate as an example of the inorganic sintering aid is mixed with the functional component (A) as a powder or an aqueous or alcoholic solution; the pH is adjusted at 3 to 4; and the mixture is further mixed with a colloid solution of colloidal silica as an example of the inorganic flocculant, thereby making the system have a pH to an approximately neutral degree. At this time, since flocculation takes place, the flocculation product is placed in a crucible or on an evaporating dish and then subjected to a heat treatment in a dryer or an electric furnace until it has become dried.

In the case where the ceramics component (C) is a combination of ceramics particles, an inorganic sintering aid and an inorganic flocculant, it is preferred that the ceramics are flocculated in a state containing the functional component (A). One example is given below. An aqueous solution of aluminum phosphate as an example of the inorganic sintering aid is added to and kneaded with particles of ceramics such as aluminum silicate, alumina, and titania so as to have a viscosity to a degree of an approximately stiff paste, and subsequently, the kneaded mixture is mixed with the functional component (A) as a powder or an aqueous or alcoholic solution (alternatively, after mixing the functional component (A) with the ceramics particles, the inorganic sintering aid is kneaded therewith). Further, an aqueous solution of aluminum phosphate is additionally mixed, if desired. And, the pH is adjusted at 3 to 4, and the mixture is further mixed with a colloid solution of colloidal silica as an example of the inorganic flocculant, thereby making the system have a pH to an approximately neutral degree. At this time, since flocculation takes place, the flocculation product is placed in a crucible or on an evaporating dish and then subjected to a heat treatment in a dryer or an electric furnace until it has become dried.

(Timing of Formulating the Finely Divided Tabular Mineral (T))

It is particularly preferred that the formulation of the finely divided tabular mineral (T) is carried out during the step of producing the composite particles of the functional component (A) and the ceramics component (C) as described above, or in the pulverization step after the composite particles have been produced.

(Proportions of the Respective Components)

While the proportions among the functional component (A), the finely divided tabular mineral (T), and the ceramics component (C) can be chosen within a wide range, it is preferred that the amount of the functional component (A) is 0.1 to 60% by weight (particularly, from 0.5 to 50% by weight), with the remainder being the finely divided tabular mineral (T) and the ceramics component (C), based on 100% by weight of the total amount of these components. When the amount of the functional component (A) is too low, the desired functionalities such as deodorizing properties, antimicrobial properties, physiological activity, and antioxidation properties are not thoroughly exhibited. On the other hand, when the amount of the functional component (A) is too high, negative features become conspicuous so that not only the functionalities do not increase exceeding a certain extent, but also the productivity of the molding is lowered, and the strength and drape are lowered.

With respect to the relationship between the finely divided tabular mineral (T) and the ceramics component (C), it is preferred that the amount of the former is 1 to 40% by weight (particularly, 2 to 30% by weight) based on 100% by weight of the total amount of the former and the latter. When the amount of the finely divided tabular mineral (T) is too low, secondary flocculation occurs, whereby the particle size tends to become large. On the other hand, when the amount of the finely divided tabular mineral (T) is too high, a balance to the functional component (A) is lost. In the latter case, for example, when the composition is used on being brought into contact with water, the elution of the functional component (A) becomes excessive so that the durability is likely impaired.

[Functional Resin Composition]

The functional resin composition according to the present invention comprises a plant-originated functional component (A), a finely divided tabular mineral (T) having a low hardness and cleavage, a ceramics component (C) other than the finely divided tabular mineral (T), and a resin (R).

With respect to the timing of formulating the finely divided tabular mineral (T), it is preferred that the finely divided tabular mineral (T) is formulated during the step of producing the composite particles of the functional component (A) and the ceramics component (C), or in the pulverization step after the composite particles have been produced, to prepare a formulation, which is then formulated into a system containing the resin (R) to prepare the resin composition. In this case, however, the finely divided tabular mineral (T) can be formulated separately before or during the preparation of the resin composition.

Examples of the resin (R) for the resin composition include forming resins, painting resins, coating resins, ink resins, adhesive resins, sealing resins, and cosmetic resins. Further, from another viewpoint, thermoplastic resins, thermosetting resins, cold-setting resins, and actinic ray-setting resins can also be used. An optimum kind of a resin is chosen and used in an optimum amount depending upon its utilization and use. The term "resin" used herein includes not only usual synthetic resins but also elastomers and rubbers as well as polymers such as cellulosic polymers.

Of these resins, the forming resins are particularly important. Accordingly, this is further described below in detail.

[Functional Molding]

(Single Molding and Composite Molding)

The functional molding according to the present invention comprises a molding of a resin (R) formulated therein with a plant-originated functional component (A), a finely divided tabular mineral (T) having a low hardness and cleavage, and a ceramics component (C) other than the finely divided tabular mineral (T).

While the molding may be a usually single molding, it may be a composite molding of a core-sheath joining type or a bimetal joining type, which is constructed of an internal component X and an external component Y, as described below.

In the case of the latter composite molding, the resin components of the internal component X and the external component Y are each comprised of a first resin ($R_1$) and a second resin ($R_2$). The first resin ($R_1$) and the second resin ($R_2$) are a resin the same as or different from each other. And, the plant-originated functional component (A), the finely divided tabular mineral (T), and the ceramics component (C) are formulated into at least one of the first resin ($R_1$) of the internal component X and the second resin ($R_2$) of the external component Y.

(Resin (R), First Resin ($R_1$) and Second Resin ($R_2$))

As the resin (R), or the first resin ($R_1$) and the second resin ($R_2$) in the case of the composite molding, melt forming resins, solution forming resins, and emulsion forming resins can be used. As described previously, the term "resin" includes elastomers and rubbers as well as polymers such as cellulosic polymers. In the case of melt forming, various melt forming methods including extrusion forming, injection forming, compression forming, and transfer forming can be employed.

Examples of the melt forming resins include polyolefinic resins, polyamide-based resins, polyester-based resins, polyvinyl chloride-based resins, polyvinylidene chloride-based resins, acrylic resins, polyurethane-based resins, polystyrene-based resins (including ABS (acrylonitrile-butadiene-styrene) resins and AS (acrylonitrile-styrene) resins), polycarbonate-based resins, ethylene-vinyl alcohol copolymer-based resins, various heat-resistant resins, and various high-strength resins. Other melt forming resins can also be used. The resin includes thermoplastic elastomers.

Of the above-exemplified resins, examples of the polyolefinic resins include homopolymers or copolymers of an olefin, comprising, as a major component, ethylene or propylene, such as low-density polyethylene, linear low-density polyethylene, medium-density polyethylene, high-density polyethylene, an ethylene-vinyl acetate copolymer, an ethylene-acrylate copolymer, ionomers, copolymers comprising ethylene as a major component with propylene or 1-butene, an ethylene-1-butene copolymer, polypropylene, copolymers comprising propylene as a major component with ethylene or $\alpha$-olefins such as 1-butene, and polyolefinic thermoplastic elastomers. Examples of the polyamide-based resins include nylon 6, nylon 66, nylon 6-66, nylon 610, nylon 612, nylon 11, nylon 12, nylon 46, nylon MXD6, and polyamide-based thermoplastic elastomers. Examples of the polyester-based resins include polyethylene terephthalate, polybutylene terephthalate, polyethylene naphthalate, and polyester-based thermoplastic elastomers. Examples of the acrylic resins include homopolymers or copolymers comprising, as a major component, a (meth)acrylate or (meth)acrylonitrile. Examples of the polyurethane-based resins include polyurethane-based thermoplastic elastomers. Examples of the polystyrene-based resins include polystyrene, high-impact polystyrene, ABS (acrylonitrile-butadiene-styrene) resins, and AS (acrylonitrile-styrene) resins.

Examples of the solution forming resins or emulsion forming resins include cellulosic polymers (such as viscose rayon, ammonia rayon, acetates, and triacetates) acrylonitrile-based polymers, polyurethane-based polymers, polyvinyl alcohol-based polymers, polyvinylidene chloride-based polymers, and polyvinyl chloride-based polymers.

The resin (R), the first resin ($R_1$), and the second resin ($R_2$) may be of a mixture of two or more resins. Further, as described previously, in the case of the composite molding, the first resin ($R_1$) and the second resin ($R_2$) may be the same as or different from each other.

In the case of the composite molding made by the melt forming, with respect to the melting points of the first resin ($R_1$) which will become the internal component X and of the second resin ($R_2$) which will become the external component Y, in many cases, the internal component X is responsible to ensuring the strength and drawing properties, while the external component Y is responsible to having the functionalities. Accordingly, it is possible to make the melting point of the first resin ($R_1$) higher (for example, 5° C. or more 10° C. or more) than that of the second resin ($R_2$). In particular, when a resin having a low melting point but capable of being subjected to melt forming is used as the second resin ($R_2$) of the external component Y, there are advantages that not only the external component Y can be made to have heat fusion properties, but also the volatilization of the active ingredient in the functional component (A) during the melt forming can be suppressed. In this case, even when the melting point of the first resin ($R_1$) is made equal to or lower than that of the second resin ($R_2$), since the functional component (A) is mainly contained in the external component Y, there is a significant advantage that the amount of the functional component (A) to be used can be made small. Accordingly, the melting point of the first resin ($R_1$) and that of the second resin ($R_2$) can be freely set up and arbitrarily determined depending upon the purpose.

(Timing of Formulating the Finely Divided Tabular Mineral (T))

With respect to the timing of formulating the finely divided tabular mineral (T), it is particularly preferred that the finely divided tabular mineral (T) is formulated during the step of producing the composite particles of the functional component (A) and the ceramics component (C), or in the pulverization step after the composite particles have been produced, to prepare a formulation, which is then formulated into the forming resin or a stock solution thereof. In this case, however, the finely divided tabular mineral (T) can be formulated separately from the functional resin (A) and the ceramics component (C) (particularly, the composite particles thereof) before or during the preparation of the forming resin or its stock solution.

(Proportions of the Respective Components)

The proportions of the respective components to be internally added to the resin (R), or the first resin ($R_1$) and/or the second resin ($R_2$) in the case of the composite molding, can be set in various ways. However, it is desired that the total amount of the functional component (A), the finely divided tabular mineral (T), and the ceramics component (C) is 1 to 50 parts by weight (preferably, 2 to 40 parts by weight) based on 100 parts by weight of the resin component. When the total amount of the functional component (A), the finely divided tabular mineral (T), and the ceramics component (C) is too low, the desired functionalities such as deodorizing properties, antimicrobial properties, physiological activity, and antioxidation properties are not thoroughly exhibited. On the other hand, when the total amount of the functional component (A), the finely divided tabular mineral (T), and the ceramics component (C) is too high, negative features become conspicuous so that not only the functionalities do not increase exceeding a certain extent, but also the productivity of the molding is lowered, and the strength and drape are lowered.

Further, with respect to the relationship among the functional component (A), the ceramics component (C), and the finely divided tabular mineral (T), it is desired that the amount of the functional component (A) is 1 to 300 pats by weight (preferably2to 200 parts by weight, and more preferably 3 to 150 parts by weight) based on 100 parts by weight of the total amount of the ceramics component (C) and the finely divided tabular mineral (T). When the amount of the functional component (A) is too low, the desired functionalities such as deodorizing properties, antimicrobial properties, physiological activity, and antioxidation properties are not thoroughly exhibited. On the other hand, when the amount of the functional component (A) is too high, a balance to the ceramics component (C) and the finely divided tabular mineral (T) is lost, leading to a disadvantage from the standpoint of cost.

Moreover, with respect to the relationship between the ceramics component (C) and the finely divided tabular mineral (T), it is preferred that the amount of the former is 1 to 40% by weight (particularly, 2 to 30% by weight) based on 100% by weight of the total amount of the ceramics component (C) and the finely divided tabular mineral (T). When the amount of the finely divided tabular mineral (T) is too low, it is impossible to prevent thoroughly an increase of the particle size of the ceramics component (C) (or the composite particles of the ceramics component (C) and the functional component (A)) due to the secondary flocculation during the forming. On the other hand, when the amount of the finely divided tabular mineral (T) is too high, the smooth moldability is likely impaired, or the secondary processing properties such as drawing properties or the physical properties of the molding are likely lowered.

(Matter To Be Taken into Consideration in the Case of Composite Molding)

The molding according to the present invention is particularly important when it is a joining type composite molding. At this time, the composite molding is a joining type composite molding constructed of an internal component X and an external component Y. Representative examples of the joining type include a core-sheath joining type and a bimetal (side-by-side) joining type. In the case of the core-sheath joining type, the internal component X is a core component, and the external component Y is a sheath component. At this time, the structure maybe any of a concentric core-sheath type, an eccentric core-sheath type, a polycentric core-sheath type, and a hollow core-sheath type. In the case of the bimetal joining type, the type is in a Y/X or Y/X/Y state (in the Y/X state, one side is made of the internal component X and the other side is made of the external component Y).

When the composite molding is of a core-sheath joining type, a suitable weight ratio of the internal component X as the core component to the external component Y as the sheath component is 30:70 to 80:20, and particularly 35:65 to 75:25. When the proportion of the sheath component is too low, since the proportion of the functional component (A) is too low, the desired functionalities are not thoroughly exhibited. Further, when the resulting molding is required to have heat adhesion, the heat adhesion is insufficient. On the other hand, when the proportion of the sheath component is too high, since the proportion of the core component X is relatively too low, the resulting molding is liable to be not satisfied from the standpoints of moldability (e.g., spinning properties, etc.), drawing properties, strength, dimensional stability, etc.

When the composite molding is of a bimetal joining type, a suitable weight ratio of the internal component X to the external component Y (in the case of a Y/X/Y state, a weight ratio of X to Y of one side) is 30:70 to 95:5, and particularly 35:65 to 90:10. Namely, the proportion of the internal component X can be made higher, as compared with the case of the core-sheath joining type.

When the composite molding is of a core-sheath joining type, a representative shape is in a filament state. Its cross-section can be made not only circular but also non-circular. As the case may be, it can also be made hollow. A thickness of the filament is arbitrary in from an extra fine fibrous state to a monofilament state (from an extra fine denier to an extra thick denier), or even up to a state close to a thicker rod.

When the composite molding is of a bimetal joining type, a representative shape is in a film or sheet state. The molding maybe slit into thin strips to form filaments. Further, the film or sheet can also be split. In addition, the molding can be formed into a container state, a plate state, or other state in a shape of various parts.

(Production of Molding and Composite Molding)

The functional molding according to the present invention is produced by providing the resin (R) formulated there in with the plant-originated functional component (A), the finely divided tabular mineral (T) having a low hardness and cleavage, and the ceramics component (C) other than the finely divided tabular mineral (T), or a stock solution thereof, for forming. As the forming method, any of a melt forming method, a solution forming method, and an emulsion forming method may be employed. A shape of the molding is arbitrary.

When the functional molding is a composite molding, the functional component (A), the finely divided tabular mineral (T), and the ceramics component (C) other than the finely divided tabular mineral (T) are previously formulated into at least one of the first resin ($R_1$) which will become an internal component X or a stock solution thereof and the second resin ($R_2$) which will become an external component Y or a stock solution thereof. Then, the formulation is subjected to co-extrusion such that the first resin ($R_1$) becomes the internal component X and the second resin ($R_2$) becomes the external component Y, to obtain a core-sheath joining type composite molding constructed of the internal component X and the external component Y, or a bimetal joining type composite molding in a Y/X or Y/X/Y state. As the forming method, any of a melt forming method, a solution forming method, and an emulsion forming method may be employed. The co-extrusion forming can be attained by discharging the both resins linearly, or in a sheet-like state, from composite dies on two or more extruders. Depending on circumstances, the both resins are formed into a net-like state by using rotating dies.

With respect to the resin (R), or the first resin ($R_1$) and/or the second resin ($R_2$) in the case of a composite molding, in the resin into which a material to be internally added is formulated, particularly in the case of melt forming, a master batch in which the concentration of the material to be internally added is high may be previously prepared and then mixed with the resin, followed by providing it for forming. If desired, in the resin composition, auxiliary agents such as antioxidants, ultraviolet light absorbers, colorants, lubricants, antistatic agents, matting agents, fluidity improvers, plasticizers, and flame retardants can be internally added. In particular, it is preferred that, in the side of the resin formulated with the material to be internally added, particularly in the case of melt forming, forming aids effective for improving the flocculation prevention or the dispersibility, inclusive of metallic soaps, are formulated together with stabilizers such as antioxidants, thereby uniform dispersion of the material to be internally added being ensured. Further, in order to improve supporting properties of the functional component (A), suitable amounts of metal ion sources such as copper salts, iron salts, calcium salts, titanium salts, aluminum salts, silver salts, tin salts, zinc salts, chromium salts, and cobalt salts can be made coexistent.

(Drawing)

In the case where a filament-state material is obtained, in many cases, drawing is carried out after the forming. While the drawing ratio is not particularly limited, when the drawing ratio is too low, the strength tends to be insufficient depending on the use. The drawing ratio is usually 3 or more, and particularly 4 or more. An upper limit of the drawing ratio is generally about 10. Further, since the drawing is not required depending on the use, the drawing is not essential. When a film-state or sheet-state material is obtained, drawing may also be carried out after the forming, if desired.

(Application and Use)

When the molding (including the composite molding) according to the present invention is in a filament state, it is unrestricted to obtain secondary products such as yarns, piles, cotton-like materials, nets, ropes, belts, woven fabrics, non-woven fabrics, and knitted fabrics, from the filament. The composite filament or secondary products thereof can be used in combination with fibers or monofilaments such as natural fibers (e.g., cotton, hemp, silk, wool, etc.), fibers or monofilaments of synthetic resins (e.g., polyesters, acrylic reins, polypropylene, polyethylene, nylons, vinylons, polyvinylidene chloride, polyvinyl chloride, polyurethane, etc.), semi-synthetic fibers (e.g., acetate fibers, etc.), regenerated fibers (e.g., rayon fibers, etc.), and inorganic fibers(e.g., glass fibers, carbon fibers, etc.), or secondary products thereof. When the molding (including the composite molding) according to the present invention is a film, a sheet, or a container, the secondary products can also be obtained by lamination or the like.

Examples of the use for which the molding (including the composite molding) or its secondary products according to the present invention are applied include interior materials of vehicles (e.g., sheet cloths, ceiling materials, flooring materials), interior materials of interiors (e.g., wall sheets, flooring materials), matting materials of interiors or vehicles (e.g., mats, carpets), filters (e.g., filters for air conditioners, air cleaners, vacuum cleaners), fan and the other moldings related thereto, inner panels of refrigerators, footwear materials, industrial materials, clothing materials, bedding-related materials, hygienic materials, medical materials, cosmetic goods (e.g. powderpuffs), daily goods, kitchen utensils, goods for bath rooms, toiletry goods, goods for pets and packaging materials.

(Heat Fused Article)

In particular, in the case of a composite molding, when the kind of the second resin ($R_2$) is chosen, or the amount of the material to be internally added is regulated, so as to impart heat fusion properties to the external component Y, heat fused articles can be obtained. For example, when textile fabrics (e.g., nets, woven fabrics, knitted fabrics) or non-woven fabrics are produced from composite filaments of a core-sheath joining type, or filaments obtained by a film of a bimetal joining type being slit into thin strips, crossover points of the filaments can be fused by heat fusion. Accordingly, it gives rise to an advantage that mesh deviation occurred during the practical use or secondary processing can be effectively prevented. Further, such the textile fabrics or non-woven fabrics can be fixed to a frame or the like.

The present invention is further described below with reference to the following Examples. In these Examples, all parts and percents are on a weight basis. The grain size was measured with a laser diffraction type grain size-measuring instrument ("SA-CP3" made by Shimadzu Corporation).

[Functional Composition]

(Preparation of Materials)

As the functional component (A), the following material was prepared.

($A_1$): 30% product of tea catechin (a tea catechin formulation originated from tea, containing about 30% in total of epigallocatechin, epigallocatechin gallate, epicatechin and epicatechin gallate)

As a raw material of the ceramics component (C), the following material was prepared.

($C_1$): Silicate aqueous solution (water glass)

As the finely divided tabular mineral (T), the following talc materials (Mohs hardness: about 1) were prepared.

($T_1$): Talc imported from Germany was used as it was.

($T_2$): Microfine talc "SG-2000" made by Nippon Talc Co., Ltd. (officially called mean particle size: 0.97 μm) was classified by sieving to obtain a fine particle side.

(Mixing Method/Method 1)

Examples 1 to 2 and Comparative Example 1

The tea catechin ($A_1$) was added to a 1N sulfuric acid solution kept at 0° C., and the 1N water glass solution ($C_1$) was separately prepared. Next, the 1N water glass solution ($C_1$) was added dropwise over several minutes into the 1N sulfuric acid solution containing the tea catechin ($A_1$) which was vigorously stirred simultaneously. At this time, the reaction solution had a temperature of 5 to 7° C., and silica was formed. The reaction mixture (composite particles of tea catechin and silica) was wet pulverized in a testing ball mill and then dehydrated. The residue was dried in vacuum in a dryer at a temperature of 50 to 60° C., was washed with running water, and then again dried. Thereafter, the residue was finely ground in a dry manner in the testing ball mill, to obtain a finely powdered functional composition.

In the above-described reaction, at the time of mixing of the water glass with the tea catechin, the mixing was carried out in such a manner that (i) talc was added in a proportion of 10% in terms of an external standard based on the total amount of the both (the amount of the water glass being on a silica basis), and (ii) 10% of the water glass (on a silica basis) was substituted with talc. For comparison, the case where no talc was mixed was experimented.

(Result)

The grain size distribution of the raw material talc and the grain size distributions of the composite particles of the functional component (A) and the ceramics component (C) in each of the case where no talc was formulated and the case where the talc was formulated are shown in table 1 and FIGS. 1 to 8. In each of the figures, (A) is a cumulative graph, and (B) is a differential graph.

TABLE 1

Figure 2:
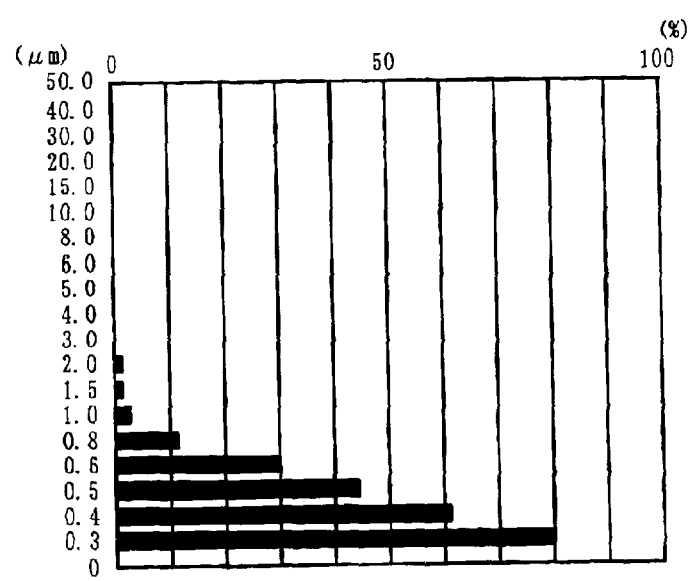
FIG. 2 is a graph showing the grain size distribution of the raw material talc ($T_2$)
Figure 2:
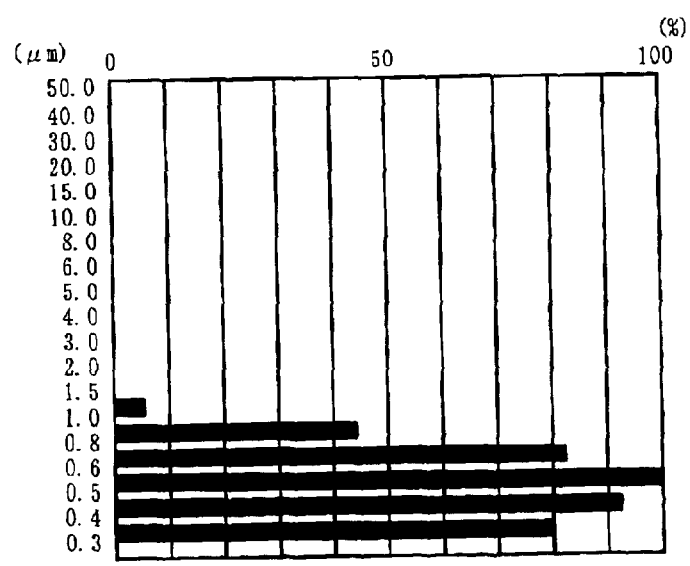
Figure 3:
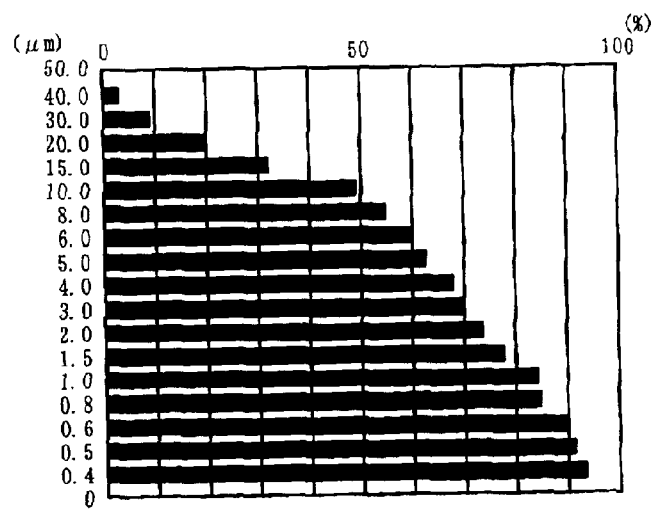
FIG. 3 is a graph showing the grain size distribution of composite particles of the functional component (A) and the ceramics component (C) when no talc is co-existent.
Figure 3:
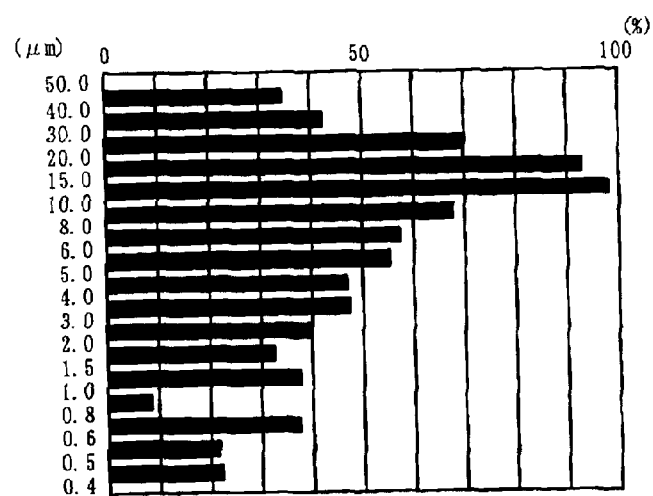
Figure 4:
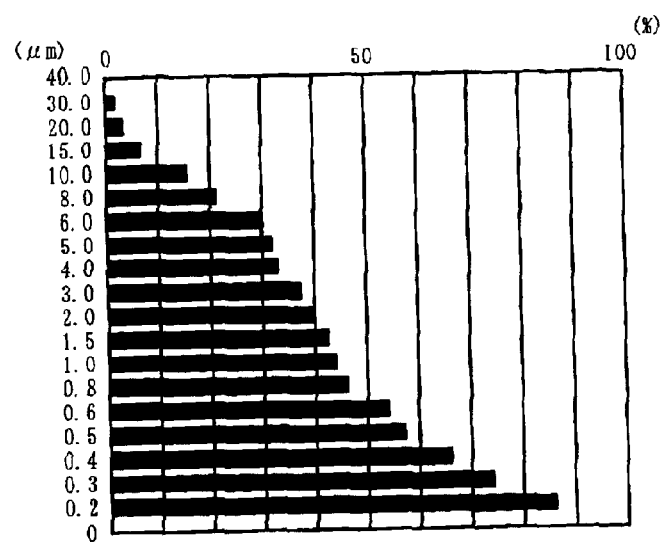
FIG. 4 is a graph showing the grain size distribution of composite particles of the functional component (A) and the ceramics component (C) when the raw material talc ($T_1$) is co-existent.
Figure 4:
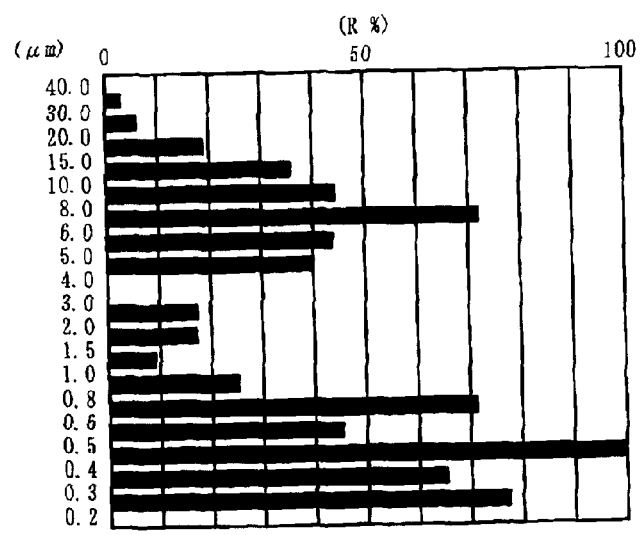
Figure 5:
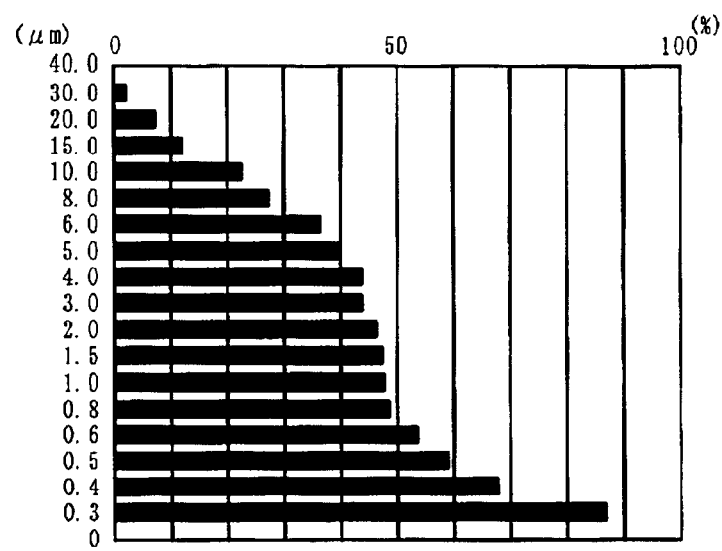
FIG. 5 is a graph showing the grain size distribution of composite particles of the functional component (A) and the ceramics component (C) when the raw material talc ($T_2$) is co-existent.
Figure 5:
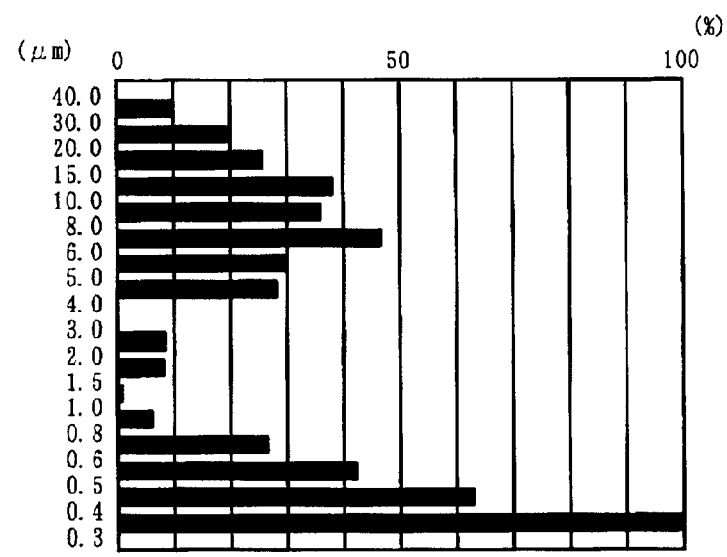

|  | Grain size distribution | | |
| --- | --- | --- | --- |
|  | Not added | ($T_1$) | ($T_2$) |
| Raw material talc | | | |
| Corresponding figure | — | FIG. 1 | FIG. 2 |
| Mean particle size (μm) | — | 0.74 | 0.47 |
| Maximum particle size (μm) | — | 2 | 2 |
| Specific surface area (m²/g) | — | 2.14 | 4.91 |
| 25% particle size (μm) | — | 1.16 | 0.65 |
| 75% particle size (μm) | — | 0.54 | 0.33 |
| 10% to raw material mixed product | | | |
| Corresponding figure | FIG. 3 | FIG. 4 | FIG. 5 |

TABLE 1-continued

Figure 6:
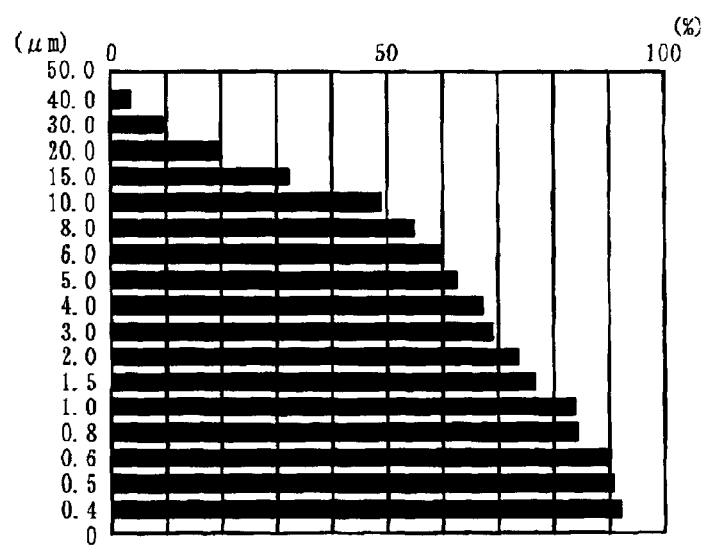
FIG. 6 is a graph showing the grain size distribution of composite particles of the functional component (A) and the ceramics component (C) when no talc is co-existent.
Figure 6:
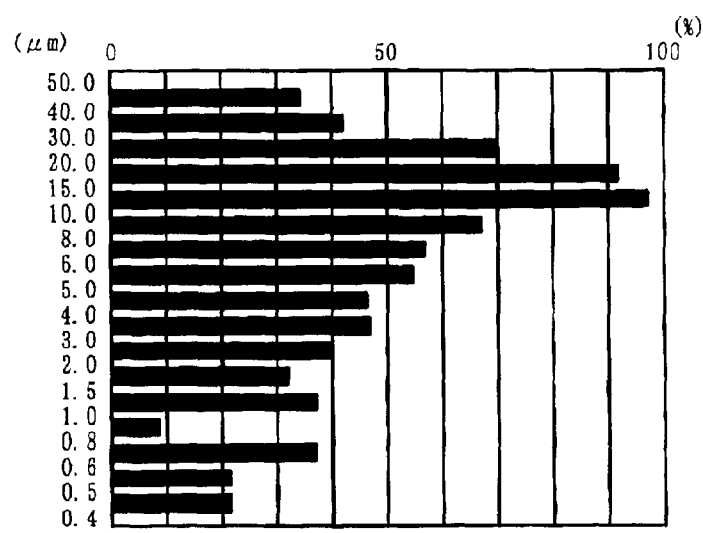
Figure 7:
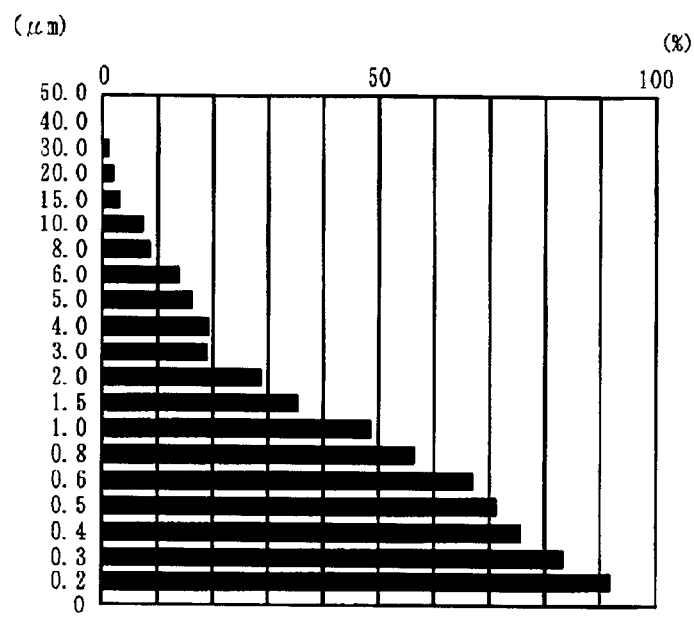
FIG. 7 is a graph showing the grain size distribution of composite particles of the functional component (A) and the ceramics component (C) when the raw material talc ($T_1$) is co-existent.
Figure 7:
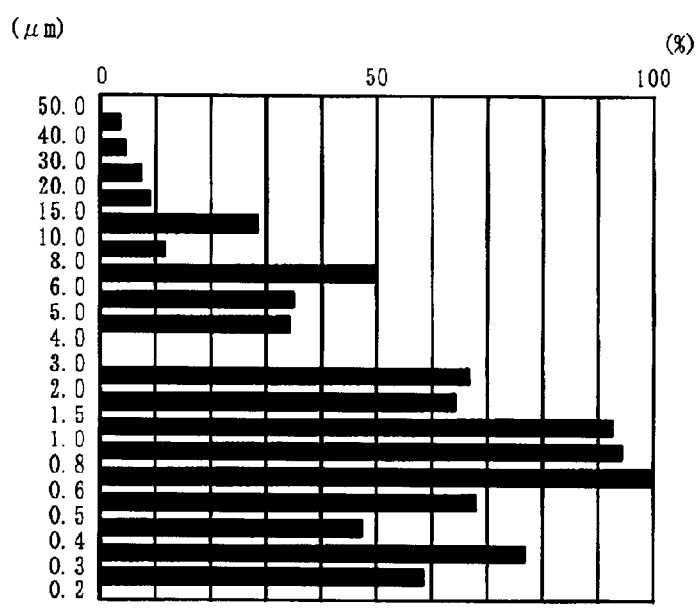
Figure 8:
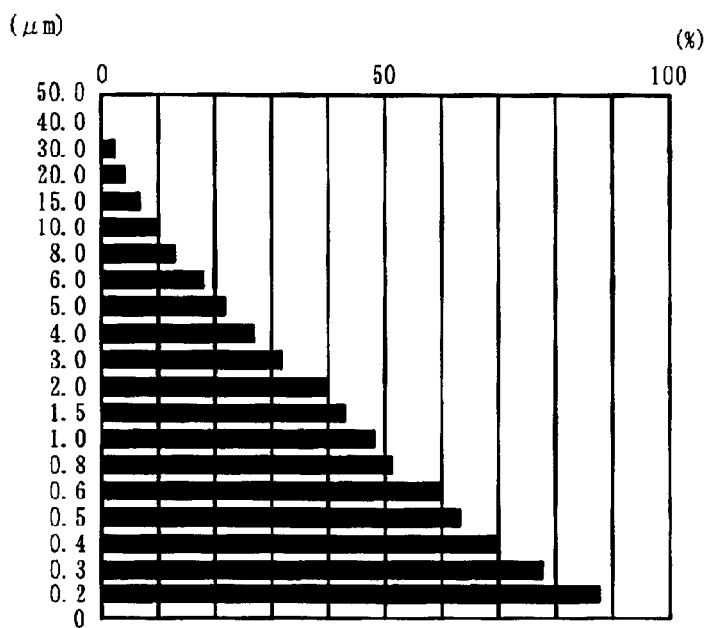
FIG. 8 is a graph showing the grain size distribution of composite particles of the functional component (A) and the ceramics component (C) when the raw material talc ($T_2$) is co-existent.
Figure 8:
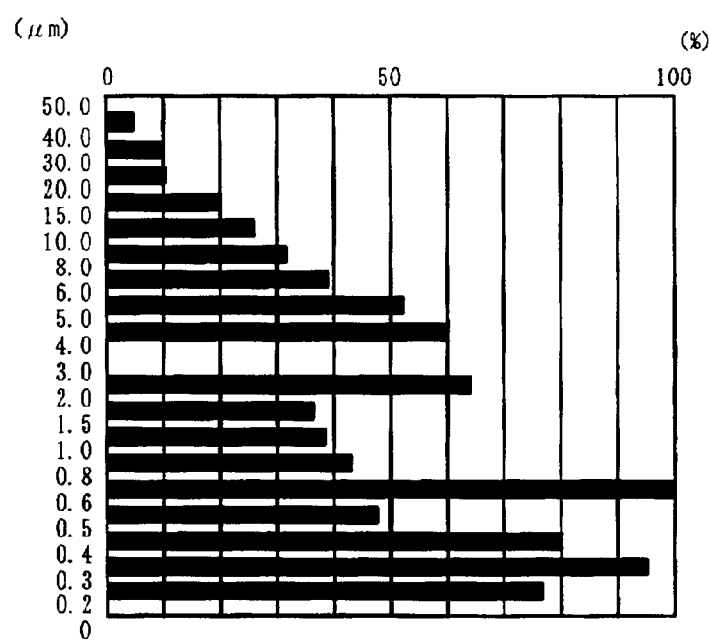

|  | Grain size distribution | | |
| --- | --- | --- | --- |
|  | Not added | (T$_1$) | (T$_2$) |
| Mean particle size (μm) | 12.82 | 0.69 | 0.76 |
| Specific surface area (m$^2$/g) | 1.07 | 4.45 | 3.14 |
| 25% particle size (μm) | 10.03 | 5.36 | 3.98 |
| 75% particle size (μm) | 1.86 | 0.29 | 0.37 |
| 10% silica substituted product to | | | |
| Corresponding figure | FIG. 6 | FIG. 7 | FIG. 8 |
| Mean particle size (μm) | 12.82 | 0.98 | 0.90 |
| Specific surface area (m$^2$/g) | 1.07 | 3.33 | 3.91 |
| 25% particle size (μm) | 10.03 | 2.36 | 2.37 |
| 75% particle size (μm) | 1.86 | 0.42 | 0.34 |

From comparison in the results as shown in the above table, it can be understood that, as compared with FIGS. 3 and 6 in which no talc is added, in FIGS. 4 and 7 in which the talc (T$_1$) is added and FIGS. 5 and 8 in which the talc (T$_2$) is added, the grain size distribution of the mixture is apparently present in the fine particle or microfine particle side, and the secondary flocculation is effectively prevented.

[Functional Resin Composition and Functional Molding]

A functional molding (composite molding) as a representative example of the functional resin composition was produced as follows.

(Preparation of Materials)

As the first resin (R$_1$), the following material was prepared.

(R$_2$): Polypropylene (PP) having a melting point of 163° C. and a specific gravity of 0.91

As the second resin (R$_2$), the following material was prepared.

(R$_1$): Polyethylene terephthalate (PET) having a melting point of 265° C. and a specific gravity of 1.4

As the functional component (A) to be internally added in the side of the second resin (R$_2$), the following materials were prepared.

(A$_1$): Tea catechin as described previously (30% product of tea catechin)

(A$_2$): Tea saponin having a purity of 70%

(A$_3$): Green tea powder (A$_4$): Powder obtained by drying a hot water-extract of green tea (A$_5$): Tannic acid having a purity of 85%

As a raw material of the ceramics component (C) to be internally added in the side of the second resin (R$_2$), the following materials were prepared.

(C$_1$): Silicate aqueous solution (water glass)
(C$_2$): Aluminum phosphate and colloidal silica
(C$_3$): Silica, aluminum phosphate and colloidal silica As the finely divided tabular mineral (T), the talc (T$_1$) and the talc (T$_2$) described previously were used.

(Preparation of Functional Component (A)-Ceramics Component (C) Composite Particles)

Composite particles comprising the functional component (A) and the ceramics component (C) were produced in the following manners. In any of the cases, the finely divided tabular mineral (T) was added during mixing of the raw material of the ceramics component (C) and the functional component (A).

(Method 1)

The raw material (C$_1$) for the ceramics component (C) was prepared in the following manner. That is, the functional material (A) was added to a 1N sulfuric acid solution kept at 0° C., and a 1N water glass solution was separately prepared. Next, the 1N water glass solution was added dropwise over several minutes into the 1N sulfuric acid solution containing the functional component (A) which was vigorously stirred simultaneously. At this time, the reaction mixture had a temperature of 5 to 7° C. The mixed solution was washed with running water for one day, and then, the water was well drained off. Thereafter, the residue was finely ground and dried in vacuum in a dryer at a temperature of 50 to 60° C., to obtain a powdered composite.

(Method 2)

The raw material (C$_2$) for the ceramics component (C) was prepared in the following manner. That is, the functional material (A) was mixed with 200 parts of an aluminum phosphate aqueous solution having a concentration of 25% to adjust a pH at 3 to 4, and the mixture was further mixed with 130 parts of a colloid solution of colloidal silica (solids content: 40%) to make the pH neutral. Since a slurry had gradually flocculated, it was placed on an evaporating dish (or in a crucible) with in a period in which it could be handled and subjected to a heat treatment by drying at 100 to 300° C. in a constant-temperature dryer or an electric furnace. A rigid, amorphous flocculation product was thus obtained. The obtained flocculation product was finely ground in an automatic mortar (or a ball mill) and classified by a sieve to obtain particles having a grain size of 100 to 325 mesh. The particles of the flocculation product were then subjected to a heat treatment in a constant-temperature dryer or an electric furnace.

(Method 3)

The raw material (C$_3$) for the ceramics component (C) was prepared in the following manner. That is, 130 parts of the functional component (A) was dry mixed with 400 parts by weight of silica having a mean particle size smaller than 325 mesh, and 200 parts of an aluminum phosphate aqueous solution having a concentration of 25% was added to and kneaded with the mixture to a degree of an approximately stiff paste. The paste was further mixed with 50 parts of a colloid solution of colloidal silica (solids content: 40%) to make the pH neutral. Since, at this time, flocculation occurred gradually, the mixture was placed in a crucible within a period in which it could be handled and then dried. Thereafter, the dried product was subjected to dehydration and hydrolysis at 100 to 300° C. and then finely ground.

Examples 3 to 9

The second resin (R$_2$) was mixed with the functional component (A)-supported ceramics component (C) obtained in Method 1, 2 or 3 as described above, together with small amounts of an antioxidant and a flocculation preventive (a dispersing agent), and the mixture was melt extruded and pelletized. The thus obtained pellets were used as the external component (sheath component) Y, and pellets of the above-described first resin (R$_1$) were used as the internal component (core component) X. The both pellets were subjected to co-extrusion under temperature conditions of 70 to 90° C. higher than the melting point of the second resin (R$_2$) with respect to the external component (sheath component) Y and under temperature conditions of 60 to 90° C. higher than the melting point of the first resin (R$_2$) with respect to the internal component (core component) X, respectively, from two extruders each equipped with a composite die, followed by drawing in a drawing ratio of about 6, to obtain a composite filament (composite molding). Thereafter, from this composite filament was prepared a non-woven fabric. The conditions are shown in Table 2.

Comparative Examples 2 and 3

The same procedures as in the foregoing Examples 3 to 9 were followed to effect co-extrusion, except omitting of the internal addition of the ceramics component (C) and the finely divided tabular mineral (T) to the second resin ($R_2$), followed by drawing in a drawing ratio of about 6, to obtain a filament (composite filament). From the thus obtained filament, a non-woven fabric was prepared. The conditions are also shown in Table 2.

Comparative Examples 4 and 5

The same procedures as in the foregoing Examples 3 to 9 were followed to effect co-extrusion, except omitting of the internal addition of the finely divided mineral (T) to the second resin ($R_2$), followed by drawing in a drawing ratio of about 6, to obtain a filament (composite filament). From the thus obtained filament, a non-woven fabric was prepared. The conditions are also shown in Table 2.

TABLE 2

| | Internal component X | External component Y | | | | Composite particles |
|---|---|---|---|---|---|---|
| | ($R_1$) | ($R_2$) | (A) | (C) | (T) | |
| Comparative Example 2 | ($R_1$): 50 parts | ($R_2$): 46 parts | ($A_1$): 3 parts | — | — | — |
| Comparative Example 3 | ($R_1$): 50 parts | ($R_2$): 46 parts | ($A_2$): 3 parts | — | — | — |
| Comparative Example 4 | ($R_1$): 50 parts | ($R_2$): 35 parts | ($A_1$): 3 parts | ($C_1$): 12 parts | — | Method 1 |
| Comparative Example 5 | ($R_1$): 50 parts | ($R_2$): 35 parts | ($A_2$): 3 parts | ($C_2$): 12 parts | — | Method 1 |
| Example 3 | ($R_1$): 50 parts | ($R_2$): 35 parts | ($A_1$): 3 parts | ($C_1$): 10 parts | ($T_1$): 2 parts | Method 1 |
| Example 4 | ($R_1$): 50 parts | ($R_2$): 35 parts | ($A_2$): 3 parts | ($C_1$): 10 parts | ($T_1$): 2 parts | Method 1 |
| Example 5 | ($R_1$): 50 parts | ($R_2$): 35 parts | ($A_3$): 3 parts | ($C_1$): 10 parts | ($T_2$): 2 parts | Method 1 |
| Example 6 | ($R_1$): 50 parts | ($R_2$): 35 parts | ($A_1$): 3 parts | ($C_2$): 10 parts | ($T_1$): 2 parts | Method 2 |
| Example 7 | ($R_1$): 50 parts | ($R_2$): 35 parts | ($A_4$): 3 parts | ($C_2$): 10 parts | ($T_2$): 2 parts | Method 2 |
| Example 8 | ($R_1$): 50 parts | ($R_2$): 35 parts | ($A_5$): 3 parts | ($C_3$): 10 parts | ($T_2$): 2 parts | Method 3 |
| Example 9 | ($R_1$): 50 parts | ($R_2$): 35 parts | ($A_1$): 3 parts | ($C_3$): 10 parts | ($T_1$): 2 parts | Method 3 |

(Test)

Each of the non-woven fabrics as prepared above was dipped in water at a normal temperature for 3 hours and then once taken out, followed by spontaneous drying. Thereafter, the filter was again dipped in water for 3 hours and then taken out, followed by spontaneous drying. The amounts of the functional component (A) before the first dipping in water and after the second dipping in water were measured by thermal analysis by means of a differential calorimeter (the temperature was elevated at a rate of 5° C./min in an electric furnace, and a heat balance (endothermic heat/exothermic heat) of the sample during the heating step and an accompanying increase or decrease in weight were analyzed). And, the non-woven fabrics before and after the water washing were subjected to a deodorizing properties test and an antimicrobial properties test under the following conditions. Further, the surface state of the composite molding (smoothness order: A>B>C), the uniform dispersibility of the particles internally added when an SEM image of the cross-section is observed (uniformity order: A>B>C), and the fineness of the particles internally added as dispersed (fineness order: A>B>C) were examined. The results obtained are shown separately in Tables 3 and 4.

(Deodorizing Properties Test)

In a 1 m³ vessel was placed an air cleaner having each of the non-woven fabrics as described above equipped therein, which could be operated externally, and five cigarettes were installed in a smoke absorber and ignited in the vessel. When the first cigarette had burnt out, the smoke absorber was stopped and when the last cigarette was burnt out, the operation of the air cleaner was started. An ammonia concentration was measured by means of a gas detector tuber 5 minutes and 30 minutes after the start of the operation. Then, a deodorizing rate was determined by how the concentration was decreased after 30 minutes, as compared with the concentration after 5 minutes(initial concentration).

(Antimicrobial Properties Test)

Each of the samples was examined for the antimicrobial properties under the following conditions.

Test item: Test for rate of decrease in number of bacteria
Test bacterium: *Staphyloccus aureus* ATCC 6538P
Test method: According to a uniform test method
Test results:
Number of planted bacteria (A):

$1.0 \times 10^5 \log A = 5.0$

Number of bacteria on non-processed cloth (B):

$1.6 \times 10^7 \log B = 7.2$ (A standard cotton cloth was used as the non-processed cloth.)

log B−log A=2.2>1.5 (the test was effective)
Increase or decrease value=log C−Log A
Difference in increase or decrease value=(log B−log A)−(log C−log A)

TABLE 3

| | Comparative Example No. | | | |
|---|---|---|---|---|
| | 2 | 3 | 4 | 5 |
| Before water washing | | | | |
| Content of (A) (%) | 2.1 | 2.0 | 2.6 | 2.6 |
| After dipping in water | | | | |
| Content of (A) (%) | 0.2 | 0.3 | 2.4 | 2.4 |
| Deodorizing rate of $NH_3$ (%) | 45 | 46 | 71 | 72 |
| Antimicrobial properties | | | | |
| Number of bacteria, log C | 6.9 | 6.9 | 3.9 | 3.9 |
| Increase or decrease value | 1.9 | 1.9 | −1.1 | −1.1 |
| Difference in increase or decrease value | 0.3 | 0.3 | 3.3 | 3.3 |
| Surface state (appearance) SEM image | A | A | B | B |
| Uniform dispersibility | A | A | B | B |
| Fineness of particles | A | A | B | B |

(For the antimicrobial properties test, 0.2 g of the sample was collected.)

TABLE 4

| | Example No. | | | | | | |
|---|---|---|---|---|---|---|---|
| | 3 | 4 | 5 | 6 | 7 | 8 | 9 |
| Before water washing | | | | | | | |
| Content of (A) (%) | 2.7 | 2.7 | 2.6 | 2.6 | 2.7 | 2.6 | 2.6 |
| After dipping in water | | | | | | | |
| Content of (A) (%) | 2.6 | 2.6 | 2.5 | 2.5 | 2.5 | 2.5 | 2.4 |

TABLE 4-continued

| | Example No. | | | | | | |
|---|---|---|---|---|---|---|---|
| | 3 | 4 | 5 | 6 | 7 | 8 | 9 |
| Deodorizing rate of NH$_3$ (%) | 75 | 75 | 73 | 73 | 74 | 72 | 72 |
| Antimicrobial properties | | | | | | | |
| Number of bacteria, log C | 3.8 | 3.9 | 3.9 | 3.9 | 4.0 | 4.2 | 3.9 |
| Increase or decrease value | −1.2 | −1.1 | −1.1 | −1.1 | −1.0 | −0.8 | −1.1 |
| Difference in increase or decrease value | 3.4 | 3.3 | 3.3 | 3.3 | 3.2 | 3.0 | 3.3 |
| Surface state (appearance) SEM image | A | A | A | A | A | A | A |
| Uniform dispersibility | A | A | A | A | A | A | A |
| Fineness of particles | A | A | A | A | A | A | A |

(For the antimicrobial properties test, 0.2 g of the sample was collected.)

It is understood from Tables 3 and 4 that, in Comparative Example 2 and 3, since the ceramics component (C) (and the finely divided tabular mineral (T)) is not co-existent in the side of the sheath component Y as the external layer, a certain amount of the functional component (A) was volatilized out during the extrusion forming and the functionalities after dipping in water were insufficient as compared with Examples. Incidentally, when drawn articles of a filament made of the second resin (R$_2$) only, in which the functional component (A) is not internally added, are used, the deodorizing rate of NH$_3$ is about 40%, and hence, a "(measured value)−40%" value is a substantial deodorizing rate. Further, it is understood that, in Comparative Examples 4 and 5, since the finely divided tabular mineral (T) is not co-existent in the side of the sheath component Y as the external layer, the surface state (smoothness on the appearance) of the composite filament as well as the uniform dispersibility of the particles of the material internally added and the fineness of the dispersed particles when the SEM image is observed are relatively inferior to those of Examples 3 to 9.

[Functional Resin Composition and Functional Molding]

A functional composition (composite molding) as a representative example of the functional resin composition was produced as follows.

As the first resin (R$_1$), the following materials were prepared.
(R$_1$): Polypropylene (PP) having a melting point of 163° C. and a specific gravity of 0.91
(R$_1$): Nylon 6 (Ny6) having a melting point of 220° C. and a specific gravity of 1.13

As the second resin (R$_2$), the following materials were prepared.
(R$_2$): Polypropylene (PP) having a melting point of 128° C. and a specific gravity of 0.91
(R$_2$): Nylon 6 (Ny6) having a melting point of 220° C. and a specific gravity of 1.13

As the functional component (A) to be internally added in the side of the second resin (R$_2$), the following material was prepared.
(A$_1$): 30% product of tea catechin as described previously As a raw material of the ceramics component (C) to be internally added in the side of the second resin (R$_2$), the following materials were prepared.
(C$_1$): Silicate aqueous solution (water glass)
(C$_4$): Sepiolite As the finely divided tabular mineral (T), the talc (T$_2$) as described previously was used.

(Preparation of Functional Component (A)-Ceramics Component (C) Composite Particles)

As to (C$_1$), composite particles with (A$_1$) were produced according to Method 1 as described above. Further, as to (C$_4$), (A$_1$) was dissolved or dispersed in water, into which (C$_4$) was then thrown, followed by mixing and drying (referred to as "Method 4", hereinafter).

Examples 10 to 14

The second resin (R$_2$) was mixed with the functional component (A)-supported ceramics component (C) obtained in Method 1 or Method 4 as described above, together with small amounts of an antioxidant and a flocculation preventive (a dispersing agent), and the mixture was melt extruded and pelletized. The thus obtained pellets were used as the external component (sheath component) Y, and pellets of the above-described first resin (R$_1$) were used as the internal component (core component) X. The both pellets were subjected to co-extrusion under temperature conditions of 70 to 90° C. higher than the melting point of the second resin (R$_2$) with respect to the external component (sheath component) Y and under temperature conditions of 60 to 90° C. higher than the melting point of the first resin (R$_1$) with respect to the internal component (core component) X, respectively, from two extruders each equipped with a composite die, followed by drawing in a drawing ratio of about 6, to obtain a composite filament (composite molding). Thereafter, from this composite filament was prepared a non-woven fabric. The conditions are shown in Table 5.

Comparative Examples 6 and 7

The same procedures as in Examples 10 to 14 were followed to effect co-extrusion, except only the functional component (A) being added internally to the side of the second resin (R$_2$), followed by drawing in a drawing ratio of about 6, to obtain a filament. From the thus obtained filament, a non-woven fabric was prepared. The conditions are also shown in Table 5.

Comparative Examples 8 to 10

The same procedures as in Examples 10 to 14 were followed to effect co-extrusion, except omitting of the internal addition of the ceramics component (C) to the second resin (R$_2$), followed by drawing in a drawing ratio of about 6, to obtain a filament (composite filament). From the thus obtained filament, a non-woven fabric was prepared. The conditions are also shown in Table 5.

TABLE 5

| | Internal component X | | External component Y | | | Composite particles |
|---|---|---|---|---|---|---|
| | $(R_1)$ | $(R_2)$ | (A) | (C) | (T) | |
| Comparative Example 6 | (PP): 50 parts | (PP): 46 parts | $(A_1)$: 3 parts | — | — | — |
| Comparative Example 7 | (Ny): 50 parts | (Ny): 46 parts | $(A_1)$: 3 parts | — | — | — |
| Comparative Example 8 | (PP): 50 parts | (PP): 35 parts | $(A_1)$: 3 parts | $(C_1)$: 12 parts | — | Method 1 |
| Comparative Example 9 | (PP): 50 parts | (PP): 35 parts | $(A_1)$: 3 parts | $(C_4)$: 12 parts | — | Method 4 |
| Comparative Example 10 | (Ny): 50 parts | (Ny): 35 parts | $(A_1)$: 3 parts | $(C_1)$: 12 parts | — | Method 1 |
| Example 10 | (PP): 50 parts | (PP): 35 parts | $(A_1)$: 3 parts | $(C_1)$: 10 parts | $(T_2)$: 2 parts | Method 1 |
| Example 11 | (PP): 50 parts | (PP): 35 parts | $(A_1)$: 3 parts | $(C_1)$: 10 parts | $(T_2)$: 2 parts | Method 1 |
| Example 12 | (PP): 50 parts | (PP): 35 parts | $(A_1)$: 3 parts | $(C_4)$: 10 parts | $(T_2)$: 2 parts | Method 4 |
| Example 13 | (Ny): 50 parts | (Ny): 35 parts | $(A_1)$: 3 parts | $(C_1)$: 10 parts | $(T_2)$: 2 parts | Method 1 |
| Example 14 | (Ny): 50 parts | (Ny): 35 parts | $(A_1)$: 3 parts | $(C_1)$: 10 parts | $(T_2)$: 2 parts | Method 1 |

(Test)

The same tests as in Examples 3 to 9 were carried out. The results obtained are shown in Tables 6 and 7. Incidentally, in Comparative Examples 6 and 7, since the ceramics component (C) is not internally added, the symbol "-" is given in the row of the SEM image in Table 6.

TABLE 6

| | Comparative Example No. | | | | |
|---|---|---|---|---|---|
| | 6 | 7 | 8 | 9 | 10 |
| Before water washing | | | | | |
| Content of (A) (%) | 2.1 | 2.0 | 2.6 | 2.6 | 2.6 |
| After dipping in water | | | | | |
| Content of (A) (%) | 0.2 | 0.3 | 2.4 | 2.4 | 2.3 |
| Deodorizing rate of $NH_3$ (%) | 45 | 46 | 71 | 72 | 68 |
| Antimicrobial properties | | | | | |
| Number of bacteria, log C | 6.9 | 6.9 | 3.9 | 3.9 | 4.1 |
| Increase or decrease value | 1.9 | 1.9 | −1.1 | −1.1 | −0.9 |
| Difference in increase or decrease value | 0.3 | 0.3 | 3.3 | 3.3 | 3.1 |
| Surface state (appearance) | A | A | B | B | B |
| SEM image | | | | | |
| Uniform dispersibility | — | — | B | B | B |
| Fineness of particles | — | — | B | B | B |

(For the antimicrobial properties test, 0.2 g of the sample was collected.)

TABLE 7

| | Example No. | | | | |
|---|---|---|---|---|---|
| | 10 | 11 | 12 | 13 | 14 |
| Before water washing | | | | | |
| Content of (A) (%) | 2.6 | 2.4 | 2.6 | 2.7 | 2.6 |
| After dipping in water | | | | | |
| Content of (A) (%) | 2.4 | 2.3 | 2.2 | 2.3 | 2.1 |
| Deodorizing rate of $NH_3$ (%) | 74 | 70 | 70 | 69 | 68 |

TABLE 7-continued

| | Example No. | | | | |
|---|---|---|---|---|---|
| | 10 | 11 | 12 | 13 | 14 |
| Antimicrobial properties | | | | | |
| Number of bacteria, log C | 3.9 | 3.8 | 3.9 | 3.9 | 4.1 |
| Increase or decrease value | −1.1 | −1.2 | −1.1 | −1.1 | −0.9 |
| Difference in increase or decrease value | 3.3 | 3.4 | 3.3 | 3.3 | 3.1 |
| Surface state (appearance) | A | A | A | A | A |
| SEM image | | | | | |
| Uniform dispersibility | A | A | A | A | A |
| Fineness of particles | A | A | A | A | A |

(For the antimicrobial properties test, 0.2 g of the sample was collected.)

Examples 15 to 17

As the resin (R), the functional component (A), a raw material of the ceramics component (C), and the finely divided tabular mineral (T), the following materials were prepared.

(R):
Polypropylene (PP) having a melting point of 163° C. and a specific gravity of 0.91
Nylon 66 (Ny66)
Polyethylene terephthalate (PET) having a melting point of 265° C. and a specific gravity of 1.4
$(A_1)$: 30% product of tea catechin
$(C_1)$: Silicate aqueous solution (water glass)
$(T_1)$: Talc imported from Germany The same procedures as in Method 1 as described above were followed to obtain composite particles comprising the functional component (A) having the ceramics component (C) and the finely divided tabular mineral (T) supported thereon.

Each of the resins (R) was mixed with the thus obtained composite particles, and the mixture was melt extruded and pelletized. The pellets were fed into an extruder and melt extruded under temperature conditions of about 80° C.

higher than the melting point of the resin (R), to obtain a filament (monofilament). Thereafter, a non-woven fabric was prepared from this filament.

In any of the cases, it was confirmed that the moldability was smooth and the surface state (smoothness) of the resulting filament was good, and that, when an SEM image of the cross-section of the filament was observed, the uniform dispersibility of the particles internally added and the fineness of the dispersed particles were good.

SEM image:
  Uniform dispersion state:A
  Fineness of the particles:A

Further, the resulting filament had superior deodorizing properties and antimicrobial properties even after dipping in water as follows.

Deodorizing rate of $NH_3$ after dipping in water:
  70 to 73%
Antimicrobial properties after dipping in water:
  Number of bacteria, log C: 3.8 to 4.2
  Increase or decrease value: −1.0 to −1.2
  Difference in increase or decrease value: 3.0 to 3.4

Example 18

The above-described 30% product of tea catechin ($A_1$) as the functional component (A), a silicate aqueous solution (water glass) ($C_1$) as a raw material of the ceramics component (C), and mica of a fine powder grade ($T_3$) as the finely divided tabular mineral (T) were prepared, respectively. Then, the same procedures as in Method 1 as described above were followed to obtain composite particles comprising the functional component (A) having the ceramics component (C) and the finely divided tabular mineral (T) supported thereon. At this time, however, finely powdered zinc oxide having a mean particle size of 0.23 μm as the ceramics component (C) was used in an amount of 10% on a silica basis together with the water glass.

As the resin (R), a polyurethane raw material composed of a polyol component and a polyisocyanate component was prepared. Further, a silicone anti-foaming agent, a catalyst, and a foaming agent (water) were prepared as aids. The composite particles as obtained above were formulated in an amount of 7% in the side of the polyol component, and expanded polyurethane (polyurethane foam) was then obtained in the customary manner.

The thus obtained polyurethane foam was good in antimicrobial properties and deodorizing properties and agreeable to the touch. Accordingly, it is suitable as, for example, a cosmetic puff and a filter.

According to the present invention, since a device for making the finely divided tabular mineral (T) having a low hardness and cleavage co-existent in a mixed system of the plant-originated functional component (A) and the ceramics component (C) is taken, a functional composition (particularly, a functional molding) in which an increase in the particle size due to the secondary flocculation of the particles in the above-described mixed system is effectively prevented can be provided.

And, when the functional composition according to the present invention is processed into a molding, extremely good results are obtained from the standpoints of moldability, post-processing properties (e.g., stretching properties, etc.), physical properties (e.g., strength, dimensional stability, etc.), appearance, and the like, since the fine particles of the additives disperse uniformly in the system of the resin. Further, superior deodorizing properties and antimicrobial properties are obtained. In addition, since the functional component (A) is fixed and made waterproof in the co-existence of the ceramics component (C), not only volatilization of the internally added functional component (A) during the forming and bleeding thereof after forming of a molding can be effectively inhibited, but also the deodorizing properties and antimicrobial properties thereof are not easily lost even when the molding is used in a state in which it is brought into contact with water so that the functionalities are maintained over a long period of time. The presence of the ceramics component (C) also contributes to the dimensional stability and heat resistance of the molding against circumferential changes such as temperature and humidity changes.

In particular, when the functional component (A) and the ceramics component (C) are contained together with the finely divided tabular mineral (T) in the external component Y of the composite molding comprising the internal component X and the external component Y, the internal addition amount of the functional component (A) can be largely reduced, leading to an advantage from the economic standpoint. Further, due to the functional component (A) present in the external component Y, superior functionalities that the functional component (A) inherently possesses, such as deodorizing properties and antimicrobial properties, are exhibited at the maximum. Moreover, strength and stretching properties are ensured by the internal component X.

Besides, since the functional component (A) is a component contained in a tea or the like, the molding is safe even when it is used in a state in which it is brought into contact with a human body.

While the present invention has been described in detail and with reference to specific embodiments thereof, it will be apparent to one skilled in the art that various changes and modifications can be made therein without departing from the spirit and scope thereof.

What is claimed is:

1. A functional molding comprising a molding of a functional resin composition which comprises:
   a plant-originated functional component (A) having deodorizing properties, antimicrobial properties, physiological properties or antioxidation properties,
   a tabular mineral (T) having a low hardness and cleavage,
   a ceramics component (C) other than the tabular mineral (T), and
   a resin (R),
   wherein at least an external surface of a final molding structure is composed of the molding of said functional resin composition so as to exhibit such functionalities.

2. The functional molding as claimed in claim 1, wherein the plant-originated functional component (A) and the ceramics component (C) are formulated in a state of composite particles of the both components.

3. The functional molding as claimed in claim 1, wherein the plant-originated functional component (A), the ceramics component (C) and the tabular mineral (T) are formulated in a state of composite particles of these components.

4. The functional molding as claimed in claim 1, wherein the plant-originated functional component (A) is at least one component selected from the group consisting of a catechin, a saponin, a tea-leaf powder, a tea-leaf extract, and tannin (tannic acid).

5. The functional molding as claimed in claim 1, wherein the ceramics component (C) is a silica gel obtained via a hydrous silicate gel, a combination of an inorganic sintering aid and an inorganic flocculent, a combination of ceramics particles other than the tabular mineral (T), an inorganic sintering aid and an inorganic flocculent, or a water-swelling clay mineral.

6. The functional molding as claimed in claim 1, wherein the molding of the functional resin composition is a filament or secondary products from the filament.

7. A joining type functional molding, which is a core-sheath joining type or bimetal joining type composite molding constructed of an internal component X and an external component Y, and which comprises a functional resin composition comprising:
- a plant-originated functional component (A) having deodorizing properties, antimicrobial properties, physiological properties or antioxidation properties,
- a tabular mineral (T) having a low hardness and cleavage,
- a ceramics component (C) other than the tabular mineral (T), and
- a resin (R),
- wherein resin components of the internal component X and the external component Y are each comprised of a first resin ($R_1$) and a second resin ($R_2$), the first resin ($R_1$) and the second resin ($R_2$) being a resin the same as or different from each other; and
- the functional resin composition is formulated into at least the second resin ($R_2$) of the external component Y.

8. The joining type functional molding as claimed in claim 7, wherein the plant-originated functional component (A) and the ceramics component (C) are formulated in a state of composite particles of the both components.

9. The joining type functional molding as claimed in claim 7, wherein the plant-originated functional component (A), the ceramics component (C) and the tabular mineral (T) are formulated in a state of composite particles of these compounds.

10. A filter for an air conditioner, air cleaner or vacuum cleaner, which filter being made of materials composed of filaments or secondary products from the filaments, wherein said material comprises a functional resin composition comprising:
- a plant-originated functional component (A) having deodorizing properties, antimicrobial properties, physiological properties or antioxidation properties,
- a tabular mineral (T) having a low hardness and cleavage,
- ceramics component (C) other than the tabular mineral (T), and
- a resin (R).

* * * * *